United States Patent

Kesling, Jr. et al.

Patent Number: 4,592,875
Date of Patent: Jun. 3, 1986

[54] ALKOXYLATED ETHER SULFATE ANIONIC SURFACTANTS FROM PLASTICIZER ALCOHOL MIXTURES

[75] Inventors: Haven S. Kesling, Jr., Drexel Hill; Hyman D. Gillman, Spring City, both of Pa.

[73] Assignee: Atlantic Richfield Company, Los Angeles, Calif.

[21] Appl. No.: 624,324

[22] Filed: Jun. 25, 1984

[51] Int. Cl.$^4$ .................. C11D 1/14; C07C 141/02
[52] U.S. Cl. .................. 252/551; 252/532; 252/545; 252/DIG. 14; 558/34
[58] Field of Search .................. 252/532, 545, 551; 260/458 R

[56] References Cited

U.S. PATENT DOCUMENTS

| | | | |
|---|---|---|---|
| 3,775,349 | 11/1973 | Tuvell et al. | 252/547 |
| 3,843,706 | 10/1974 | Weil et al. | 260/458 |
| 3,931,271 | 1/1976 | Baumann et al. | 260/458 |
| 3,956,401 | 5/1976 | Scardera et al. | 260/458 R |
| 4,259,215 | 3/1981 | Murata et al. | 252/528 |
| 4,395,364 | 7/1983 | Murata et al. | 252/526 |

FOREIGN PATENT DOCUMENTS

| | | |
|---|---|---|
| 2226988 | 12/1973 | Fed. Rep. of Germany. |
| 84399 | 6/1980 | Japan. |
| 738538 | 10/1955 | United Kingdom. |
| 797119 | 6/1958 | United Kingdom. |

OTHER PUBLICATIONS

T.P. Matson, *Soap and Chemical Specialties*, Nov. 1963.
J. Clebicki et al., *Synthesis and Surface Activity of Sodium Polypropylated High Alcohol Sulfates, Tenside Detergents*, 17, 130–134 (1980).
Martin J. Schick, Nonionic Surfactants, p. 118, Marcel Dekker, Inc., N.Y. (1967).

*Primary Examiner*—Prince E. Willis
*Attorney, Agent, or Firm*—Michael S. Jarosz

[57] ABSTRACT

Mixtures of alkoxylated ether sulfate anionic surfactants of this invention are prepared by conventional procedures, e.g., oxyalkylation with propylene oxide or 1,2-butylene oxide of a plasticizer range linear or branched "oxo" alcohol; optionally followed by oxyalkylation with ethylene oxide or with a mixture of ethylene oxide and higher alkylene oxide; sulfation of the alkoxylated product; and neutralization of the sulfated derivative. The alkoxylated ether sulfate anionic surfactant compositions of the present invention are liquids which exhibit superior detergency to polyester fabrics, excellent hard water stability, low foaming, low odor, and exhibit excellent compatibility with non-ionic and other surfactants in detergent formulations. The compositions of the invention are prepared as concentrates containing high proportions of active ingredients which are capable of being diluted with water without formation of a gel phase or lumps and as surfactants exhibit properties comparable to commercial surfactants prepared from "detergent" range alcohols.

17 Claims, No Drawings

4,592,875

ALKOXYLATED ETHER SULFATE ANIONIC SURFACTANTS FROM PLASTICIZER ALCOHOL MIXTURES

BACKGROUND OF THE INVENTION

1. Field of the Invention

The present invention relates to novel mixtures of different alkoxylated ether sulfate anionic surfactants based on plasticizer range linear or branched alcohols, and to concentrated aqueous surfactant compositions based on such mixtures. More particularly, this invention relates to certain novel relatively short chain ether alcohol sulfate anionic surfactants produced by propoxylation or butoxylation of "plasticizer" range primary or branched "oxo" alcohols, optionally followed by alkoxylation with ethylene oxide or with a mixture of ethylene oxide and propylene oxide or butylene oxide, followed by sulfation and neutralization. The compositions of the invention are prepared as concentrates containing high proportions of active ingredients which are capable of being diluted with water without formation of a gel phase or lumps and as surfactants exhibit properties comparable to commercial surfactants prepared from "detergent" range alcohols.

2. Description of the Prior Art

During the last several years, primary "detergent" range alcohol (i.e. fatty alcohol) ethoxylated sulfates have been used extensively in large volume surfactant applications such as light duty liquid dishwashing detergents, concentrated laundry detergents, hard surface cleaners, and as textile surfactants. The advantages of the ethoxylated ether sulfates over the previously employed alcohol sulfates include ready synthesis, increased solubility, and insensitivity to hard water (see for example T. P. Matson, *Soap and Chemical Specialties*, November 1963).

Propoxylated and butoxylated alcohol ether sulfate anionic surfactants have been disclosed in the prior art, but are not known to have been employed in commercial applications. A substantial portion of prior art disclosing such surfactant compositions deals only with "detergent" (i.e. containing about 12 to 18 carbon atoms) as disclosed, for example, in Weil et al. U.S. Pat. No. 4,383,706, and with short oxypropylene chains generally between about 1 and 3 propylene oxide units, as disclosed for example in Tuvell et al U.S. Pat. No. 3,775,349. Although 8 and 10 straight chain carbon alcohols containing greater than 3 oxypropylene units have been studied, J. Chlebicki et al, *Synthesis and Surface Activity of Sodium Polyoxypropylated Higher Alcohol Sulfates*", Tenside Detergents, 17, 130-134, (1980), the authors conclude that these materials are generally inferior surfactants as compared with propoxylated surfactants prepared from "detergent" range alcohols.

Fabric softeners employable in the laundry wash, rinse or dryer cycle are desired for commercial application. Furthermore, because of the inconvenience of rinse and dryer cycle application, the industry is attempting to develop softeners that are compatible with wash cycle applications. Cationic quaternary ammonium salts, which are used commercially in fabric softening applications, cannot be used in the wash cycle with anionic surfactants. It is believed that the cationic and the anionic materials complex and precipitate, thus reducing detergency. Although wash cycle detergent/fabric softner formulations have been prepared from non-ionic surfactants and cationic softeners, these formulations lack the detergent power that can be obtained when an anionic surfactant is used as the detergent.

Mixtures of surfactants have also been prepared and sold for a wide variety of industrial and domestic applications. Such compositions often are required in fluid form, and it is desirable that they should contain as high a proportion of active material as possible, in order to reduce the cost of storage and transport. However, in the case of most surfactant mixtures, it has generally been impossible to obtain a fluid composition to concentrations above about 30 to 50 percent and higher, by weight, of active ingredient, and further, depending upon the nature of the mixture, small amounts of water, i.e. up to about 10 percent may depress the melting point slightly while larger quantities of water result in the formation of a rigid gel rather than a fluid solution as a result of a phase change. Hence, it has generally been found that as the total concentration of surfaces active ingredient in a dilute solution approaches a critical level, which usually ranges between about 30 to 50 percent by weight or higher, the viscosity of the solution begins to rise, causing difficulty in preparing and handling the solution. At the critical level the solution sets into an immobile gel or phase separation occurs.

It has sometimes been possible to increase the concentration of active ingredient by addition of viscosity modifiers or co-solvents, such as alcohols, which act as thinners thereby lowering the viscosity of the solution and inhibiting the formation of gels, and permitting the obtainment of higher concentrate solutions. However, such co-solvents are normally effective in producing substantial increases in the attainable concentration when they are present in readily large quantities, which solvents, at these concentrations, constitute a fire hazard and may adversely affect the properties of the product compositions for many of its desired end uses and/or increase the cost of the product.

As used herein, the term "active concentration" will be used to denote the total concentration of "active" i.e., surface active, ingredients in the aqueous anionic surfactant composition.

Aqueous solutions of sulfates of alkoxylated fatty alcohols, generally containing from 10 to 24 carbon atoms in the alcohol chain, such as sulfated ethoxylated lauryl alcohol, or mixtures containing lauryl alcohol derivatives, have been employed in cosmetic, toiletry and other detergent compositions. In general, these compositions are supplied at about 30 percent active ingredient, but in the interest of economy and transport and packaging, high concentrations of the order of 50 to 70 percent, are also commercially available. At these high concentrations they have the texture of a thick paste. In the final formulation, these compositions are normally present in an amount of less than about 30 percent active ingredients in aqueous solution. As indicated above, unfortunately, upon dilution of these concentrates with water, rather than the viscosity diminishing as might be expected, the viscosity begins to substantially increase; for example, the sodium salt of the sulfate of a di-ethoxylated derivative of a commonly used mixture of alcohols containing between 10 and 18 carbon atoms having a concentration of 60% active matter, the balance being water, has a viscosity of approximately 17,000 centipoises. Upon dilution to 45% active matter, the viscosity increases to greater than 500,000 centipoises. Upon further dilution, the viscosity drops until at the concentration used in shampoos, for example, it again becomes liquid.

Although it has been possible in some instances to employ such concentrates without the incorporation of viscosity modifiers, such as increase in the viscosity during dilution, naturally contributes substantial problems for the formulator. Such problems include the formation of lumps and gels which are themselves only difficulty soluble on attempted further dissolution. In order to avoid these problems, viscosity modifiers have been incorporated as above indicated, in aqueous concentrates of sulfates of ethoxylated fatty alcohol so as to maintain viscosity of the solution at high concentrations at a level such as to maintain the viscosity at a level such that the solutions are reasonably free flowing and are easily diluted through any required concentration. In addition to modifying the viscosity of these solutions, it is also necessary that any additive employed should not prevent or hinder the effect of thickeners conventionally used, such as sodium or ammonium salts, which may be incorporated in the finished formulation in order to provide an acceptable consistency. At present, this problem is being reduced by incorporating into the concentrated aqueous sulfate of ethoxylated fatty alcohol, an alcohol of low molecular weight such as isopropranol or ethanol. However, the use of such alcohols is disadvantageous in that having high vapor pressure their odor is detectable in the finished formulation and, further, such compositions may constitute a fire hazard as above indicated.

An object of the present invention is to provide aqueous solutions of admixtures of anionic surfactants based on plasticizer range linear or branched alcohols.

A further object of the present invention is to provide water and organic solvent soluble anionic surfactant admixture compositions characterized as being free of unpleasant odor and exhibiting excellent detergency and stability in hard water and low foaming properties.

Another object of this invention is to provide highly active concentrated anionic surfactant, free-flowing admixture compositions requiring no added solubilizing agents and which are capable of being diluted with water without formation of undesired highly viscous lumps or gel phase.

Other objects of this invention are readily apparent to those skilled in the art from the following description.

DESCRIPTION OF THE INVENTION

The alkoxylated ether sulfate anionic surfactant admixture compositions of the present invention correspond to the formula:

RO—CH$_2$CH(R')O—$_m$Z$_n$SO$_3$M        (Formula I)

wherein R is a straight or branched hydrocarbon alkyl radical containing of from about 4 to 11 carbon atoms; R' is a member selected from the group consisting of methyl and ethyl; m is an integer of from 3 to 12, preferably 6 to 10; Z is an oxyethylene group or a random mixture of oxyethylene groups and oxyalkylene groups present in the radical—[CH$_2$CH(R')O], the molar ratio of oxyethylene to oxyalkylene groups in said mixture being such that the total molar ratio of oxyethylene to oxyalkylene groups in said formula is from about 1:1 to 1:10; n is an integer of from 0 to 4; and M is hydrogen, an alkali metal, an alkaline earth metal; ammonia or a primary, secondary, tertiary amine or quaternary ammonium ion, said admixture being characterized as containing at least two of said surfactants present in a mole ratio within the range of from about 10:1 to 1:10, generally between about 4:1 and 1:4. Preferred components of the admixture compositions of the invention conform to the above-identified formula wherein R is a straight chain alkyl radical containing from about 8 to 10 carbon atoms; when R' is methyl, m is 4 to 9, and when R' is ethyl, m is 3 to 6, n is 0, and M is an alkali metal, such as sodium or potassium, or ammonium. It is to be understood that additional components conforming to Formula I, above, may also be present as part of the surfactant admixture composition, and when present, generally constitute up to ten percent by weight, of the composition. In addition, the surfactant compositions of the invention may also contain minor amounts, up to about two percent, each by weight, of alkoxylated sulfates of C$_4$ or C$_{12}$ alcohols.

The concentrated aqueous surfactant compositions of the invention comprise at least about 5%, but not more than about 50%, generally not more than about 40%, by weight of water, and an active mixture comprising at least two of the alkoxylated ether sulfate anionic surfactants conforming to Formula I above, present in a ratio of between about 1:10 and 10:1, preferably between about 1:2 and 2:1, said compositions being characterized as being capable of dilution with water to any concentration of active ingredient without formation of a gel phase or lumps.

In accordance with the present invention, it has been surprisingly found that admixtures of alkoxylated ether sulfate anionic surfactants based on plasticizer range linear and/or branched oxo-alcohols exhibit unexpectedly improved detergency characteristics for textile materials and fabric softening properties, as compared with the individual alkoxylated alcohols, or with commercially available alkoxylated fatty alcohol derived surfactants. In addition, the anionic surfactant compositions of the present invention have been found to exhibit important advantages as detergent intermediates compared with anionic surfactant compositions produced from ethylene oxide alone. Hence, it has been found that the physical properties of the alkoxylated ether sulfate admixture compositions of the invention contrast with properties of commercially available ethoxylated ether sulfates derived from "detergent" or fatty alcohols, which are solids at concentrations of greater than about 60 percent, whereas the alkoxylated ether sulfate surfactant admixtures of the invention are liquids at concentrations as high as 90 percent and higher.

In accordance with the present invention, it has further been found that aqueous solutions of admixtures of alkoxylated ether sulfate anionic surfactants present in a wide range of active concentration may be prepared; these solutions exhibit viscosity and dilution properties that enable them to be prepared as concentrates and diluted with water when preparing a detergent formulation containing active concentration of surfactant conventionally employed, without detracting from the properties of such formulations, i.e. are readily diluted with water to any required or desired concentration without forming gels or lumps and are reasonably free-flowing. Hence, such solutions are, in general, characterized by having a viscosity, at 25° C., of less than about 1,000 cps, and preferably, of less than about 100 cps. In addition, the ethoxylated ether sulfates derived from fatty alcohols require a solvent, as above pointed out, in order to maintain a solution even at the 50 to 60 weight percent concentration; in contrast, no solvent is required to dissolve or maintain the alkoxylated ether sulfate surfactant admixtures of the invention. These differences in physical properties provide the surfactant admixture composition with a significant economic advantage associated with shipping, storage and in end use applications, as compared with the aforementioned compositions.

Furthermore, the alkoxylated alcohol ether sulfate anionic surfactant admixtures of the invention are equivalent to or better than commercially employed surfactant compositions as detergents, for example, dodecyl benzene sulfonate-based surfactants, non-ionic surfactants, and commercially available ethoxylated ether sulfates, such as Neodol ® 25-3S. Moreover, the alkoxylated ether sulfate admixtures of the invention are substantive to cotton and are employable as wash cycle fabric softeners; the results obtained are comparable with those obtained using commercially available wash cycle fabric softening formulations.

Moreover, the alkoxylated ether sulfate surfactant admixtures of the invention are stable and exhibit good detergency at hard water hardness of 500 ppm or higher and also have been shown to be exceptional lime soap dispersants, as compared with commercially available dodecyl benzene sulfate compositions. Other advantages characteristic of the surfactant compositions of the present invention include good primary biodegradability, excellent solubility and good detergency in both hot and cold water, excellent solubility in organic solvents such as toluene, hexane, and 1,1,trichloroethane, noncorrosiveness to mild steel and most polymers, and the ability to be spray dried without volatility loss, good alkaline stability, and excellent compatibility with non-ionic and other surfactants in detergt formulations. The alkoxylated ether sulfate surfactants of the present invention, while being anionic character, have many of the desirable properties of a nonionic surfactant.

The alkoxylated ether sulfate anionic surfactant components may be straight or branch-chain, depending upon the percursor alcohol employed in preparation of the surfactant composition. In general, anionic surfactant admixtures in which the alkyl group R in above Formula I is straight-chain are preferred, especially surfactant components containing between 8 and 10 alkyl groups as R.

Illustrative alkoxylated ether sulfate anionic surfactants which serve as components of the admixture compositions of the present invention include:

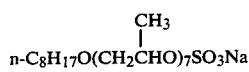

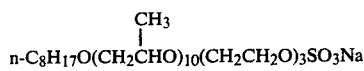

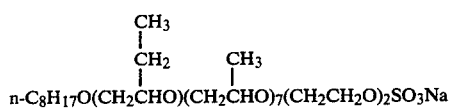

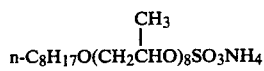

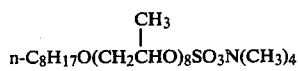

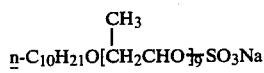

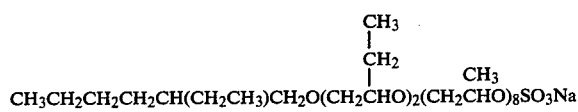

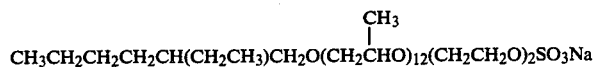

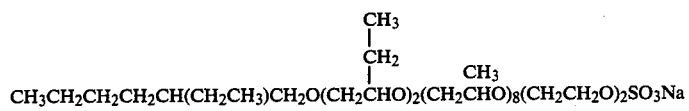

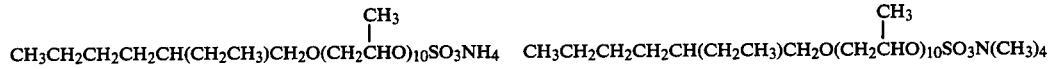

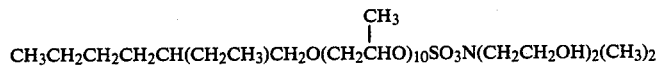

-continued

CH₃CH₂CH₂CH₂CH(CH₂CH₃)CH₂O(CH₂CHCH₃O)₁₀SO₃N(CH₂CH₂OH)₄

CH₃CH₂CH₂CH₂CH(CH₂CH₃)CH₂O(CH₂CHCH₃O)₁₀SO₃K   CH₃CH₂CH₂CH₂CH(CH₂CH₃)CH₂O(CH₂CHCH₃O)₁₀SO₃N(CH₂CH₂OH)₃H i-C₅H₉O(CH₂CHCH₃O)₁₂SO₃Na   i-C₉H₁₉O(CH₂CHCH₃O)₁₀SO₃Na

The surfactant admixture compositions of the invention may be prepared by known methods, for example, by alkoxylation of an admixture of plasticizer range linear or oxo-alcohols, or mixture thereof containing of from 5 to 11 carbon atoms, present in the molar proportions corresponding to the admixture desired product. Alkoxylation of the alcohol admixtures is effected at elevated temperatures, generally between about 70° and 150° C., preferably between about 90° and 100° C. at pressure ranging from atmospheric to about 500 psig, preferably between about 50 and 100 psig, in the presence of an alkaline catalyst, such as an alkali metal hydroxide, illustratively, potassium hydroxide, present in a concentration ranging from between about 0.01 and 1 weight percent preferably between about 0.2 and 0.3 weight percent of the reactant. In general, a controlled amount of propylene oxide or 1,2-butylene oxide, or an admixture thereof, is slowly contacted with the alcohol reactant, which optionally may be preheated to a liquid state, over a reaction time, generally ranging up to about 20 hours, in an amount sufficient to form the desired oxyalkylated reaction product mixture.

In general, sufficient alkylene oxide is employed in the alkoxylation reaction to effect preparation of an alkoxylated derivative admixture having an average number of alkylene oxide units per molecule in the surfactant product of between 3 and 12, and preferably between 6 and 10. Optionally, if desired, in a second step, as is known in the art, for example, from Martin J. Schick, "Nonionic Surfactants", pp. 118, Marcel Dekker, Inc. New York (1967), ethylene oxide may be added to the reaction product of the first alkoxylation step to produce an ethylene oxide "tipped" product having a primary hydroxyl group, or alternatively, this second alkoxylation step may be effected by use of a mixture of ethylene oxide and propylene oxide or 1,2-butylene oxide, thereby producing an alkoxylated ether characterized by a block or random structure, under the reaction conditions specified above for the first alkoxylation reaction. In general, when ethylene oxide alone is added, approximately one to four moles of ethylene oxide is added, and when a mixture of ethylene oxide and propylene oxide or 1,2-butylene oxide is employed, the molar ratio of ethylene oxide to such higher alkylene oxide range from about 1:1, preferably from about 2:1 to about 5:1. The amount of oxides employed when the second alkoxylation is performed is such that each component of the resultant product admixture contains a total molar ratio of oxyethylene groups to oxypropylene or oxybutylene groups from about 1:1 to about 1:10, and preferably from about 1:2 to about 1:4.

If desired, the oxyalkylation of the alcohol admixture may be carried out in a suitable solvent, illustratively, an aromatic hydrocarbon such as toluene, benzene, ethers such as tetrahydrofuran and the like. Other solvents employable for this purpose include aliphatic hydrocarbons containing from about 5 to 12 carbon atoms, such as heptane, hexane, octane and the like, thereby obviating the toxic associations connected with use of aromatic hydrocarbon solvents, if employed. It is also necessary to ensure that the alcohol reactant is free of water, and hence, vacuum stripping of the starting material may be employed in conventional manner.

Alcohols which may be employed in the preparation of the alkoxylated intermediates in production of the surfactant compositions of the present invention are commercially available and may be obtained, for example, by the Ziegler process, as disclosed in F. Asinger, "Mono-olefin Chemistry and Technology" Pergamon Press, N.Y. (1968), or by; the oxo process, as disclosed, for example in Richard F. Heck, "Organotransition Metal Chemistry" Academic Press, New York (1974); hence, suitable alcohols include any primary, linear plasticizer or branched oxo-alcohol mixture containing of from about 4 to 11, preferably 8 to 10 carbon atoms in the chain. Illustrative suitable alcohols include n-butanol n-hexanol; n-octanol; 3-methyl butanol; 1-heptanol; 2-nonanol; 1-nonanol; 2-ethylhexanol; isomeric oxo nonanol admixtures and n-decanol.

The alkoxylated alcohol admixture obtained is converted to the corresponding sulfate admixture typically by reaction with chlorosulfonic acid, sulfur trioxide, or concentrated sulfuric acid in accordance with well known procedures such as disclosed in U.S. Pat. Nos. 2,187,244 and 3,931,271. In general, for example, when sulfation is effected by use of chlorosulfonic acid, a slight excess of chlorosulfonic acid diluted with equal portion volumes of a solvent such as methylene chloride, is slowly added to a solution of oxyalkylated oligomer, present in equal volume portion, in methylene chloride over a period of 2 hours. The temperature is held at 10° to 25° C. using an icebath and nitrogen sweep. Sulfation with chlorosulfonic acid in the absence of solvent is also possible if good control over heat transfer is maintained.

The surfactant admixture compositions of the invention are of high quality characterized as being essentially free of unpleasant odor. This is a significant advantage as compared with those alkoxylated surfactant compositions produced from Ziegler type alcohols which have been alkoxylated soley by ethylene oxide. It has been reported that such compositions derived from Ziegler alcohols exhibit a high and objectionable odor level. In contrast, the use of propoxylation or butoxylation in production of the desired surfactant compositions of the invention eliminates the undesired odor associated with alkoxylated surfactants which are solely ethoxylated products. This observation is rationalized by considering the relative reactivity of ethylene oxide and higher alkylene oxide such as propylene oxide or butylene oxide with Ziegler alcohols; in the case of ethylene oxide alone, the product ether alcohol from ethoxylation is a primary alcohol, whereas, in the case of said higher alkylene oxides, the product is a secondary ether alcohol which is considerably less likely to react relative to the starting alcohol or impurities which are primary alcohols. Thus, all the starting alcohol impurities are alkoxylated, e.g. propoxylated, before further propoxylation of the secondary alcohol product occurs, and hence, propoxylation, of these impurities significantly decreases volatility and thus, reduces odor.

Following sulfation, the alkoxylated ether sulfate composition corresponding to Formula I, above, wherein M is hydrogen, is neutralized by known methods, for example, by reaction with: an alkali metal hydroxide, such as sodium hydroxide, as the most preferred, potassium hydroxide and lithium hydroxide; an alkaline earth metal hydroxide such as magnesium hydroxide, calcium hydroxide, cesium hydroxide, rubidium hydroxide or aluminum hydroxide; ammonia or a substituted amine derivative thereof. Typical substituted amine derivate reactants employable for this purpose include ammonia, triethanolamine, triisopropanolamine and the like. Normally the neutralization agent is employed in concentration ranging from between about 25 and 50 weight percent to produce a product with a pH of between about 7 and 10, preferably between 7 and 7.7. If desired, a solvent such as a lower alkanol, illustratively ethanol or isopropanol in a concentration of at least 10%, when employed, may be used.

The following examples will serve to illustrate the practice of the invention, but they are not intended to limit it to the details described herein. Parts and percentages are by weight, temperatures, are in degrees Centigrade, unless otherwise specified.

EXAMPLES

A. Preparation of Alkoxylated Derivative of Appropriate Alcohol

All reactions were carried out in a 2-gallon oil heated stirred stainless steel autoclave. A 0.25 percent catalyst solution was prepared using the appropriate alcohol admixture and potassium hydroxide by preheating at 75°–100°. Water was removed under vacuum and the catalyst solution was charged hot under dry nitrogen into the autoclave. The remaining alcohol was added to the reactor followed by purging with dry nitrogen. The reactor was heated to 95° and dry alkylene oxide in the appropriate stoichiometry was slowly added over a period of 24–48 hours using a pressure demand control valve system to control the addition rate. A reference pressure was set at 60 psig, and if the reactor pressure dropped below this pressure the control valve opened and more alkylene oxide was charged to the reactor. When the pressure increased to greater than 60 psig, the valve closed. The alkylene oxide was contained in a hoke that was suspended on a weight load cell, thereby permitting the charging of the correct amount of alkylene oxide. Since the hoke had a 80 psig nitrogen pressure head, the overall reactor pressure increased to 80 psig when all the liquid alkylene oxide was pushed out of the load cell hoke into the reactor. When the reaction was complete, the product was removed hot from the reactor and was treated with Magnesol ® (4 grams per 250 grams of product) for 2 hours at 120° in order to remove the catalyst. The resulting product was vacuum filtered through a Cellite bed at 60°–80° to provide the pure oligomeric polyol. Hydroxyl number, VPO molecular weight, GPC analysis, and $^{13}C$ NMR were primarily used to characterize the product oligomers.

B. Preparation of Sulfate as a Derivative

1. Sulfation with Chlorosulfonic Acid and Neutralization

A slight excess of chlorosulfonic acid diluted 50/50 with methylene chloride was slowly added to a solution of oxyalkylated admixture oligomer (50/50) in methylene chloride over the course of two hours. The temperature was held at 10°–25° using an ice-bath and a nitrogen sweep (approximately 2–5 liters/minute) was used to remove hydrochloric acid from the reaction zone. After the addition was complete, the mixture was allowed to stir an additional 1–2 hours at 35°–40°. The excess methylene chloride solvent was stripped from the sulfated product via rotary evaporation prior to neutralization. The product was neutralized with 50 percent sodium hydroxide to a pH of 7.5–9.0, and the neutralized product was cooled overnight at 10° C. and filtered to remove sodium chloride and sodium sulfate. The product was extracted with petroleum ether to remove unreacted oligomer and was stripped to remove water and any remaining solvent. Both of the above purification steps (i.e., filtration and extraction) are optional and need not be always used. The final alkoxylated ether sulfate anionic surfactant admixture product is a liquid at active concentration of 90 wt.% or greater.

2. Sulfation with Sulfur Trioxide and Neutralization

Liquid sulfur trioxide diluted with an air stream was slowly added over a two hour period at 25° in an amount sufficient to provide 65% propoxylated oligomer conversion to the appropriate alkoxylated, e.g. propoxylated polyol in admixture methylene chloride solvent. By holding the conversion low, acid build up and unsaturation due to elimination could be prevented. The sulfur trioxide incorporated into the $SO_3Na$ containing surfactant was determined by titration with Hyamine ®-1622 (to methylene blue end-point) and the unreacted sulfur trioxide was determined by scrubbing through sodium hydroxide followed by simple acid-base titration. At the end of the sulfation run, the temperature was increased to 35° for one hour and air was bubbled through the solution to ensure that all the unreacted sulfur trioxide was removed or reacted. The product was neutralized with 50 percent sodium hydroxide to a pH of 8.0 followed by extraction with petroleum ether to recover the unreacted propoxylated polyols for recycle.

EXAMPLES 1–18

A number of surfactants of the invention were prepared using the synthetic procedures outlined in paragraphs A and B-1 above. Their properties are set forth in Table I below.

TABLE I

| | Properties of Alkoxylated Alcohol Sodium Sulfates and Other Surfactants | | | | | | |
|---|---|---|---|---|---|---|---|
| Example No. | Alcohol or Surfactant | Alkylene Oxide/ Units | Draves Wetting[6] (Sec) | Surface Tension[7] (Dynes/cm) | Concentration (% Active) | Viscosity (cps) | Detergency[8] Polyester |
| | | | | | | | % SR | % D |
| 1 | Epal ® 108 | propylene oxide/5 | 8.5 | 30.4 | 92.1 | 402 | 58.6 | 40.4 |
| 2 | Epal ® 810[(2)] | propylene oxide/5 | 11.7 | 33.3 | 81.4 | 376 | 68.6 | 64.8 |

TABLE I-continued

Properties of Alkoxylated Alcohol Sodium Sulfates and Other Surfactants

| Example No. | Alcohol or Surfactant | Alkylene Oxide/ Units | Draves Wetting[6] (Sec) | Surface Tension[7] (Dynes/cm) | Concentration (% Active) | Viscosity (cps) | Detergency[8] Polyester % SR | Detergency[8] Polyester % D |
|---|---|---|---|---|---|---|---|---|
| 3 | Epal ® 610[3] | propylene oxide/5 | 10.6 | 35.0 | 90.2 | 245 | 85.9 | 82.7 |
| 4 | Epal ® 610 | propylene oxide/8 | — | — | 90.2 | — | 85.9 | 82.7 |
| 5 | Epal ® 810 | propylene oxide/8 | — | — | 90.0 | — | 90.0 | 90.6 |
| 6 | Epal ® 108 | propylene oxide/8 | — | — | 98.4 | — | 82.4 | 78.0 |
| 7 | Epal ® 810 | propylene oxide/12 | — | — | 96.2 | — | 83.3 | 81.7 |
| 8 | Epal ® 108 | propylene oxide/10 | — | — | 94.3 | — | 83.8 | 83.8 |
| 9 | Epal ® 108 | propylene oxide/12 | — | — | 92.7 | — | 84.1 | 81.5 |
| 10 | Epal ® 108 | propylene oxide/8[9] | — | — | 91.7 | — | 78.9 | 77.2 |
| 11 | Iso-C$_9$"oxo" mixture | propylene oxide/5 | 10.0 | 34.6 | 93.6 | — | 75.4 | 61.9 |
| 12 | Iso-C$_9$"oxo" mixture | propylene oxide/10 | 5.7 | 34.1 | 92.8 | — | 73.9 | 71.3 |
| 13 | Epal ® 108[1] | ethylene oxide/5 | >1200 | 38.1 | 73.5 | 257 | 0 | 0 |
| 14 | 2-Ethylhexanol | ethylene oxide/5 | >1800 | 42.5 | — | — | 0 | 0 |
| 15 | N—Octanol | propylene oxide/8 | 31.0 | 34.2 | — | — | 75.0 | 68.3 |
| 16 | N—Heptanol | propylene oxide/8 | 29.2 | 39.2 | — | — | 53.1 | 50.1 |
| 17 | N—Octanol | propylene oxide/5 | 210.0 | 38.1 | — | — | 66.2 | 41.9 |
| 18 | Neodol 25-3S Ethoxylated Surfactant[4] | — | 18.0 | 34.2 | 58.9 | — | 74.8 | 72.8 |
| 19 | UltraWet ® 60K Dodecyl-benzene Sulfonate | — | — | — | 64.0 | — | 62.3 | 62.3 |
| 20 | Neodol 25-7 Non-Ionic Surfactant[5] | — | — | — | 33.7 | — | 72.4 | 70.6 |

Notes:
[1]A "plasticizer" grade alcohol comprised of about 56 percent octanol, 42.9 percent decanol, 0.3 percent hexanol and 0.7 percent dodecanol.
[2]A "plasticizer" grade alcohol comprised of about 44.3 percent octanol, 54.5 percent decanol and 0.3 percent hexanol.
[3]A "plasticizer" grade alcohol comprised of about 40.0 percent octanol, 55.4 percent decanol, 3.6 percent hexanol and 0.9 percent dodecanol.
[4]An anionic sulfate surfactant derived from the ethoxylation with three units of ethylene oxide of a detergent grade alcohol comprised of $C_{12-15}$ carbon atom aliphatic alcohol.
[5]A nonionic surfactant derived from detergent grade $C_{12-15}$ alcohol.
[6]Draves wetting is measured on a 0.1 wt % solution at room temperature (77° F.).
[7]Surface Tension is measured on a 1% solution at 25° C.; Kraft Points is 1°.
[8]Terg-o-tometer test with: Speed = 125 rpms; Temperature = 120° F.; Time = 10 minutes/ Surfactant concentration = .15 wt %; hardness = 150 ppm; 4" × 6" cloth - each wash batch used 5 soiled and 3 clean polyester fabric; the panels used in determining evaluation were coated with standard pad applied airborne/dust sebum soil.

$$\% \text{ Soil Removal (SR)} = \frac{R_L \text{ Soil BW} \times 100}{R_L \text{ Unsoiled} - R_L \text{ Soil BW}}$$

$$\% \text{ Detergency (D)} = \frac{R_L \text{ Soil Aw} - (R_L \text{ Redeposition BW-AW})}{R_L \text{ Redeposition} - R_L \text{ Soil BW}} \times 100$$

$R_L$ = Reflectance (L Scale)
AW = After Wash
BW = Before Wash
[9]The propoxylated surfactant obtained by propoxylation of Epal ® 108 alcohol was end-capped with three units of ethylene oxide.

The results set forth in Table I, comparing typical surfactant admixture compositions of the present invention (Examples 1–12) with commercially available surfactants (Examples 18–20), as well as with a number of surfactants derived from ethoxylation of specific alcohol substrates or surfactants derived from propoxylation of individual alcohols (Examples 11–17), demonstrate the obtainment of at least equal or improved surface activity, wetting, and detergency with respect to polyester fabric. These results additionally show the obtainment of highly concentrated, i.e. above 90% active, liquid, non-viscous compositions of the invention as compared with commercially available compositions of substantially lesser activity.

EXAMPLES 21–27

The experimental procedure outlined under Examples 1–7 was followed to prepare alkoxylated derivative admixtures of the invention, while varying the base employed for neutralization, to demonstrate the counter-ion effect upon surface active properties; and surface tension, Draves wetting and detergency were obtained in the same manner as in Table I, above. The results are set forth in Table II, below.

TABLE II

| Example No. | Alcohol/ Surfactant | Alkylene Oxide/ Units | Counter-ion (M)+ | Draves Wetting (Sec) | Surface Tension (Dynes/cm) | Detergency Polyester % SR | Detergency Polyester % D |
|---|---|---|---|---|---|---|---|
| 21 | Iso-C$_9$ "OXO" Mixture | propylene oxide/5 | +Na | 10.0 | 34.6 | 75.4 | 69.7 |
| 22 | Iso-C$_9$ "OXO" Mixture | propylene oxide/5 | +K | 9.3 | 31.3 | 84.6 | 81.3 |
| 23 | Iso-C$_9$ "OXO" Mixture | propylene oxide/5 | +NH$_4$ | 13.0 | 30.6 | 80.5 | 77.9 |
| 24 | Iso-C$_9$ "OXO" Mixture | propylene oxide/5 | +NH$_3$CH$_2$CH$_2$OH | 22.0 | 33.8 | 79.1 | 69.7 |
| 25 | Iso-C$_9$ "OXO" Mixture | propylene oxide/5 | +NH$_3$CH$_2$CHOH | 29.0 | 34.9 | 75.8 | 75.3 |
| 26 | Iso-C$_9$ "OXO" Mixture | butylene oxide/5 | +Na | 5.8 | 30.2 | 81.5 | 78.5 |

TABLE II-continued

| Example No. | Alcohol/ Surfactant | Alkylene Oxide/ Units | Counter- ion (M)+ | Draves Wetting (Sec) | Surface Tension (Dynes/cm) | Detergency Polyester %SR | %D |
|---|---|---|---|---|---|---|---|
| 27 | Neodol 25-3S[1] | | +Na | 18.0 | 34.6 | 71.0 | 68.4 |

[1]Commercially available ethoxylated $C_{12}$-$C_{15}$ fatty alcohol

It can thus be seen that valuable and highly desirable alkoxylated ether sulfate anionic surfactant admixtures which exhibit excellent detergency, viscosity characteristics, wetting capabilities, hard water stability, and surface activity have been provided. Further, these compositions are characterized as being of high active concentration, and may be readily diluted with water without formation of gels, lumps and highly viscous compositions of low flowability.

Although the alkoxylated ether sulfate anionic surfactant admixture described in the foregoing have useful detergent properties per se, it is generally preferred to use them in combination with other detergent active compounds and with various adjuvants such as hydrotopes, typically cumene, xylene, and toluene sulfonates, perfumes, pH modifiers, inorganic salts, bacteriastats, dyes, solvents such as alkanols and carbitols, typically ethanol, isopropanol, methyl carbitol and ethyl carbitol and the like. Further, if desired, the surfactant compositions of the invention may be employed with other adjuvents specific to desired applications such as carboxymethyl cellulose, optical brighteners, corrosion inhibitors, alkaline builders, and the like, as is well known in the art.

Our invention has been described and illustrated by reference to specific embodiments thereof, and the examples illustrate the best mode presently known for carrying out the invention. It should be noted, however, that variations of these procedures are feasible and many such variations would be obvious to those skilled in the art in view of the disclosures contained herein.

We claim:

1. A water-soluble, liquid admixture of alkoxylated ether sulfate anionic surfactants corresponding to the formula:

$$RO[CH_2CH(R')O]_m Z_n SO_3 M$$

wherein R is a straight or branched hydrocarbon alkyl radical containing of from about 4 to 11 carbon atoms; R' is a member selected from the group consisting of methyl and ethyl; m is an integer of from 6 to 12; Z is a oxyethylene group or a random mixture of oxyethylene groups and oxyalkylene groups present in the radical —$CH_2CH(R')O$—, the molar ratio of oxyethylene to oxyalkylene groups in said mixture being such that the total molar ratio of oxyethylene to oxyalkylene groups in said formula is from about 1:1 to 1:10; n is an integer of from 0 to 4; and M is hydrogen, an alkali metal, an alkaline earth metal; ammonium or a primary, secondary, or tertiary amine or quaternary ammonium ion, said admixture of surfactants being characterized as containing at least two of said surfactants present within a molar ratio of between about 4:1 and 1:4.

2. The anionic surfactant admixture of claim 1 wherein R' is methyl.

3. The anionic surfactant admixture of claim 1 wherein R is an alkyl radical containing of from 6 to 10 carbon atoms and R' is methyl.

4. The anionic surfactant admixture of claim 3 wherein M is an alkali metal.

5. The anionic surfactant admixture of claim 3 wherein M is sodium.

6. The anionic surfactant admixture of claim 3 wheren M is potassium.

7. The anionic surfactant of admixture claim 3 wherein M is ammonium.

8. The anionic surfactant of claim 3 wherein M is hydrogen.

9. The anionic surfactant admixture of claim 2 wherein m is an integer of from 6 to 10; n is 0 and M is sodium.

10. The anionic surfactant admixture of claim 9 wherein the admixture is further characterized as being obtained by the (i) propoxylation of a substantially straight chain alcohol admixture comprised of between about 40 and 60 percent, by weight, of octanol, 40 and 60 percent, by weight, of decanol, and up to about 5 percent, by weight, of hexanol; (ii) sulfation with a member selected from the group consisting of chlorosulfonic acid and sulfur trioxide; and (iii) neutralization with sodium hydroxide.

11. The anionic surfactant admixture of claim 9 wherein the admixture is further characterized as being obtained by the (i) propoxylation of a substantially branched chain admixture selected from the group consisting of isononyl alcohols and 2-ethyl hexanol; (ii) sulfation within a member selected from the group consisting of chlorosulfonic acid and sulfur trioxide; and (iii) neutralization with sodium hydroxide.

12. An aqueous, liquid surfactant concentrate composition comprising at least about 5%, but not more than 50%, by weight, of water, and the active anionic surfactant admixture of claim 1.

13. An aqueous, liquid surfactant concentrate composition comprising at least about 5%, but not more than 50%, by weight, of water, and the active anionic surfactant admixture of claim 3.

14. An aqueous, liquid surfactant concentrate composition comprising at least about 5%, but not more than 50%, by weight, of water, and the active anionic surfactant admixture of claim 5.

15. An aqueous, liquid surfactant concentrate composition comprising at least about 5%, but not more than 50%, by weight, of water, and the active anionic surfactant admixture of claim 9.

16. An aqueous, liquid surfactant admixture concentrate composition comprising at least about 5%, but not more than 50%, by weight, of water, and the active anionic surfactant admixture of claim 10.

17. An aqueous, liquid surfactant admixture concentrate composition comprising at least about 5%, but not more than 50%, by weight, of water, and the active anionic surfactant admixture of claim 11.

* * * * *